US005569844A

United States Patent [19]

Sowerby

[11] Patent Number: 5,569,844
[45] Date of Patent: Oct. 29, 1996

[54] METHOD AND APPARATUS FOR DETERMINING THE PARTICLE SIZE DISTRIBUTION, THE SOLIDS CONTENT AND THE SOLUTE CONCENTRATION OF A SUSPENSION OF SOLIDS IN A SOLUTION BEARING A SOLUTE

[75] Inventor: Brian D. Sowerby, Kareela, Australia

[73] Assignee: Commonwealth Scientific and Industrial Research Organisation, Campbell, Australia

[21] Appl. No.: 379,673

[22] PCT Filed: Aug. 16, 1993

[86] PCT No.: PCT/AU93/00419

§ 371 Date: Feb. 8, 1995

§ 102(e) Date: Feb. 8, 1995

[87] PCT Pub. No.: WO94/04907

PCT Pub. Date: Mar. 3, 1994

[30] Foreign Application Priority Data

Aug. 17, 1992 [AU] Australia ................... PL4150

[51] Int. Cl.6 .............. G01N 15/02; G01N 23/10; G01N 29/18; G01N 29/20
[52] U.S. Cl. .............. 73/61.75; 73/32 A; 73/865.5; 378/53
[58] Field of Search ............. 73/61.71, 61.75, 73/61.42, 61.79, 61.49, 32 A, 32 R, 865.5, 597, 599, 601; 378/53

[56] References Cited

U.S. PATENT DOCUMENTS

| 3,710,615 | 1/1973 | Johnson et al. ................ 73/61.75 |
| 3,779,070 | 12/1973 | Cushman et al. ............... 73/865.5 |
| 3,794,836 | 2/1974 | Hinckfuss ..................... 378/53 |
| 4,414,841 | 11/1983 | Porenski, Jr. et al. ........... 73/61.75 |
| 4,506,543 | 3/1985 | Kamp ......................... 378/53 X |
| 4,706,509 | 11/1987 | Riebel ........................ 73/865.5 |
| 5,058,432 | 10/1991 | Morkun et al. ................. 73/61.75 X |
| 5,121,629 | 6/1992 | Alba .......................... 73/865.5 X |
| 5,359,897 | 11/1994 | Hamstead et al. ............... 73/597 |
| 5,368,716 | 11/1994 | Kikuta ........................ 73/61.49 X |

FOREIGN PATENT DOCUMENTS

| 1773128 | 11/1971 | Germany . |
| 2229810 | 10/1990 | United Kingdom . |

OTHER PUBLICATIONS

Patent Abstracts of Japan, P-854, p. 13, JP-A-63-308558 (Electric Power Dev. Co. Ltd.) 15 Dec. 1988.
Patent Abstracts of Japan, P-854, p. 102, JP-A-63-309850 (Electric Power Dev. Co. Ltd.) 16 Dec. 1988.
Patent Abstracts of Japan, P-974, p. 109, JP-A-1-233367 (NKK Corp), 19 Sep. 1989.

*Primary Examiner*—Hezron E. Williams
*Assistant Examiner*—Michael J. Brock
*Attorney, Agent, or Firm*—Kenyon & Kenyon

[57] ABSTRACT

A measurement system (45) includes a tank (46) having an inlet and outlet (47, 48) through which a sample (49) flows prior and subsequent to measurement. A stirrer (50) disposed near the base of tank (46) maintains a well mixed solution within the tank. Two immersion probes (52, 53) extend downwardly into the tank and include respective support tubes (54, 55) and sensor portions (56, 57). The sensor portions include respective gamma-ray transmission gauges and four pairs of ultrasonic transducers operating at different frequencies. Accordingly, probes (52, 53) allow the measurement of attenuation and velocity of high and low frequency ultrasound through the sample as well as measurement of attenuation of electromagnetic radiation through the sample. These measurements are utilized to derive an estimate of the solute concentration, particle size distribution, concentration of solids and suspension and the solute concentration of the sample.

15 Claims, 9 Drawing Sheets

METHOD AND APPARATUS FOR DETERMINING THE PARTICLE SIZE DISTRIBUTION, THE SOLIDS CONTENT AND THE SOLUTE CONCENTRATION OF A SUSPENSION OF SOLIDS IN A SOLUTION BEARING A SOLUTE

TECHNICAL FIELD

This invention relates to a method and apparatus for determining the particle size distribution, the solids content and the solute concentration of a suspension of solids in a solution bearing a solute. Advantageously, the invention is applicable for use in industrial processes such as in the precipitation section of the Bayer process.

BACKGROUND ART

In certain industrial processes, such as the precipitation section of the Bayer process, it is desirable to monitor the particle size distribution of solids in a slurry or suspension under dynamic conditions and to determine the deviation of the actual particle size distribution from that desired. The invention will be herein described with particular reference to the Bayer process but is not limited to that use.

In the precipitation section of the Bayer process alumina is extracted and purified from bauxite. Bauxite is crushed and ground, then digested at elevated temperature (104°–230° C.) and pressure in a strong solution of caustic soda (80–110 g $Na_2O$/liter). The residue, known as red mud, is separated from the solution by countercurrent decantation and filtration. After cooling, the solution is supersaturated with respect to alumina. In the precipitation (crystallization) process the supersaturated solution is seeded with recycled alumina trihydrate fines and agitated in large tanks. The productivity of the Bayer process is limited by the slowest step, the precipitation of the alumina trihydrate from the liquor. After precipitation, the alumina is calcined at temperatures up to 1300° C. and sold typically for commercial smelting to aluminium.

The goal of the precipitation section is to maximise alumina yield whilst maintaining product quality (particle size and strength) and seed balance. Control variables in precipitation are temperature, starting alumina/caustic ratio, seed charge, caustic concentration, holding time and impurity levels (particularly organics).

It is desirable to minimise the proportion of fines (minus about 45 microns as well as minus about 20 microns) in product alumina. These fines cause dust problems during handling operations and they cause significant flow and segregation problems in aluminium smelters. Fines are generated in the precipitation, calcining and handling stages of the plant. Improved control of the precipitation stage should produce less fines in precipitator product and a stronger alumina (Sang, J. V., "Factors affecting the attrition strength of alumina products", Light Metals, 1987, 121–127) which will in turn generate less fines in downstream calcining and handling.

The optimisation of alumina precipitation would benefit from the development of suitable on-line particle size analysers to monitor the proportions of both coarse and fine alumina at a number of cut-off points, for example at 20, 45, 75 and 100 microns. Measurements preferably need to be made under the following plant conditions: caustic concentration 150 to 250 g NaOH/liter; temperature 60° to 80° C.; solids content up to 35 wt %; scale build-up rates of about 10 mm /week; and variable air bubble concentration and size distribution.

At present there are no commercially available on-line particle size monitors capable of this measurement.

The conventional method of measuring particle size distribution is to remove samples from the streams of interest and to perform screen analyses on these samples. A screen analysis involves a series of procedures by which a measurement is made of the proportion of the sample that remains on each of several screens having progressively smaller openings of known size. While this kind of measurement can provide a reasonably accurate determination of particle size distribution above about 45 microns, it is representative only of the particular sample taken, and cannot accurately and reliably indicate either the average condition in the flowstream over a period of time, or the changes that occur between sampling. Also the method is not applicable to fine fractions below 45 microns, and is labour intensive and time consuming and therefore does not lend itself to either manual or automatic control.

There are three commercially available on-line particle size analysers which are finding significant use in the control of grinding circuits in the metalliferous mineral industry. However, these analysers are not suitable for use in alumina precipitation circuits, primarily because of air bubbles, scaling, caustic and high temperatures. These three on-line particle size analysers are based on ultrasonic attenuation (Autometrics PSM-400), a scanning laser microscope (Lasentec Par-Tec 200/300) and a reciprocating caliper (Outokumpu PSI-200). Alternative systems based on laser diffractions operate only on highly dilute solutions (<5 g solids/liter) and are not suitable for on-line use. The onstream laser scanning microscope (the Lasentec Par-Tec 200/300) does not require dilution of the process stream (J. Hokanson, "In-line particle size measurement for improved process control in the mineral processing industry", Light Metals 1991, 39–42). In this analyser, the sample is scanned at constant speed by a high intensity laser beam and the reflected light is measured. Particles outside the focus of the laser beam are discriminated against on the basis of the rise time of the reflected light pulse. The main disadvantages of this technique are:

(i) it measures a very small sample and so flow conditions at the window affect the results;

(ii) it does not operate in the presence of scale;

(iii) it requires a transparent fluid; and (iv) the sensitivity to surface characteristics (shape and reflectivity) and air bubbles, while also being inaccurate on fine particles.

The reciprocating caliper device (Outokumpu PSI-200) uses a simple and direct measurement technique to determine the largest particle in the caliper. The device will not operate in the presence of scale and it cannot measure the fine particle size fractions.

The ultrasonic device (Autometrics PSM-400) determines the fraction of particles of size above a particular cut point (usually about 75 microns) by measuring ultrasonic attenuation at two frequencies. One frequency is chosen where attenuation is not greatly affected by particle size and the second frequency is chosen to be sensitive to particle size. Combining these results allows one to derive a single point on the size distribution curve, provided that the shape of the size distribution curve remains fairly constant. Measurements can be made on water-based slurries containing up to 30 wt % solids although air bubbles need to be eliminated before measurement.

The Autometrics PSM system, however, is not suitable for use in alumina precipitation plants as it is unable to correct for changes in caustic concentration, it is unable to determine the concentration of fine (minus 20 micron) particles and there is no correction for the effect of scaling or temperature.

Figure 1:
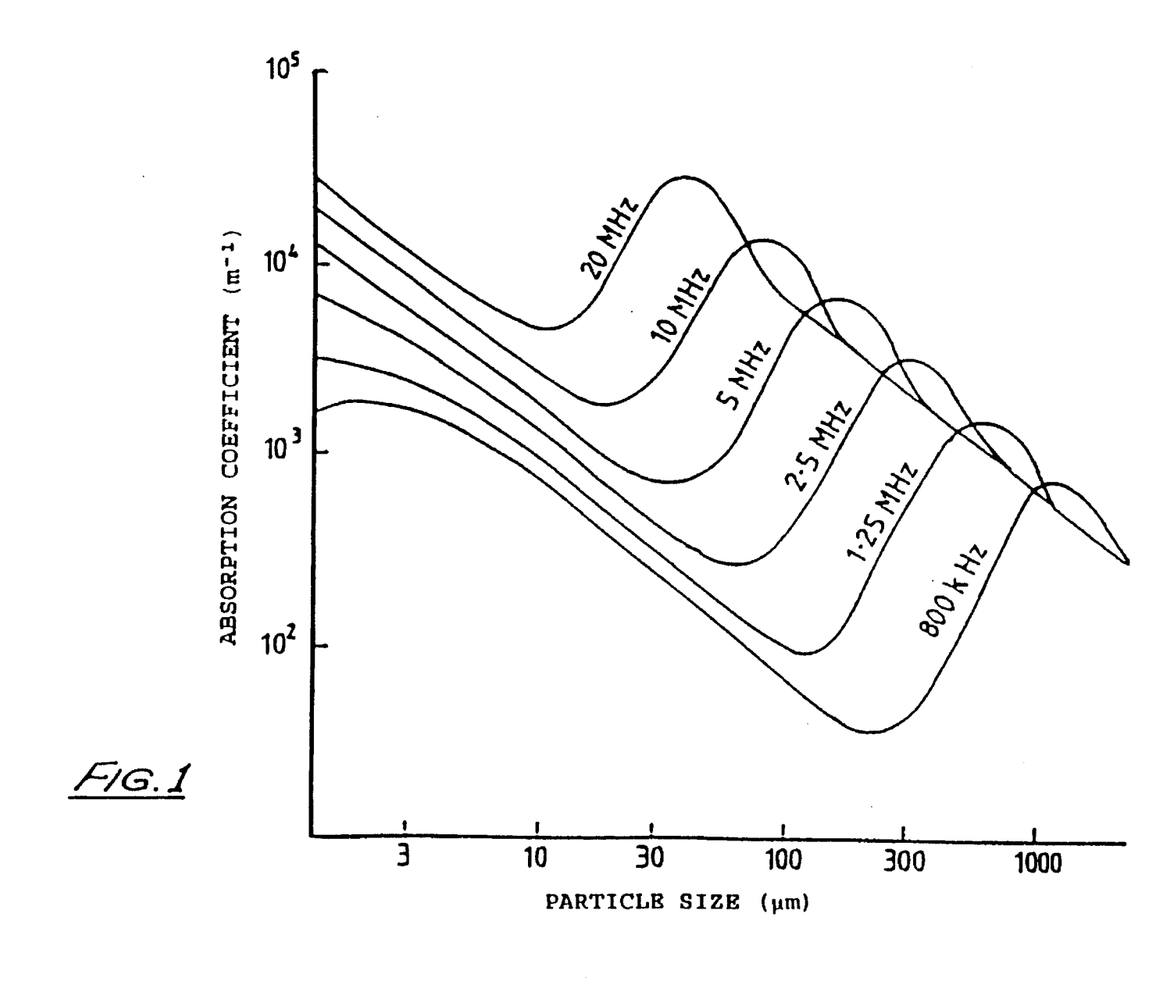
FIG. 1 is a graph showing the calculated dependence of the absorption coefficient on particle size at different frequencies for suspensions of quartz in water.

The theory for ultrasonic theory attenuation methods shows that viscous and scattering losses provide the two main regions where direct calculation of size from the observed attenuation is possible. If a pulsed beam of ultrasonic waves is transmitted through a sample slurry stream, the intensity of the transmitted beam is given approximately by:

$$A = A_0 \exp(-2\alpha x) \quad (1)$$

where $2\alpha$=absorption coefficient $A_0$=initial intensity of wave x=distance travelled by wave The absorption coefficient is determined by two primary mechanisms, viscous and scattering losses. Viscous losses are associated with the relative movement of liquid and solid. The particles vibrate in response to the ultrasonic wave but with a phase lag and different amplitude. Extremely small particles tend to move in phase with the fluid and losses are very small. As size increases the particles tend to lag more and more behind the movement of the fluid and the loss per particle increases, but at the same time the solid-liquid interface area and therefore the loss per unit mass decrease. These opposing factors result in a viscous absorption maximum below about 3 microns particle size for frequencies above 800 kHz, as shown in FIG. 1 in which the calculated dependence of the absorption coefficient on particle size at different frequencies is plotted for suspensions in water (Riebel, U. and Loffler, F., U.S. Pat. No. 4,706,509 Nov. 17, 1987). The ratio of particle density to fluid density and the fluid velocity are also important in determining viscous loss.

The second loss mechanism is the scattering of energy due to the absorption of a small amount of energy from the directed beam by each particle, and its subsequent radiation away from the point of absorption.

For ultrasonic wavelengths much greater than particle radius, it is possible to express the relationship between $\alpha$ and the properties of the solids and liquid by the equation:

$$2\alpha = c \left( \frac{k^4 r^3}{6} + k(\gamma - 1)^2 \frac{s}{s^2 + (\gamma + d)^2} \right) \quad (2)$$

where r=particle radius $\lambda$=wavelength of ultrasonic wave, c=volume concentration of solids, k=angular wavenumber of ultrasonic wave in water, $\gamma$=ratio of densities of particles and water, $\omega$=angular frequency of ultrasonic wave, $$s = \frac{9}{4\beta r} \left( 1 + \frac{1}{\beta r} \right),$$

where $$\beta = \left( \frac{\omega}{2v} \right)^{1/2},$$

$v$=kinematic viscosity of water, $$d = \frac{1}{2} + \frac{9}{4\beta r}$$

This equation is valid up to about 20% solids, above which the dependence on c becomes more complex.

The first term in equation (2) represents the attenuation due to scattering loss and the second due to viscous loss. For a given frequency, at very small particle sizes the viscous loss is predominant but as the size increases it becomes insignificant and the scattering loss becomes important.

For the case where $\lambda \ll 2\pi r$ (generally for particles well above 100 μm diameter and for frequencies of 1–10 MHz), diffraction losses become important and equation (2) must be replaced by the expression $$2\alpha = \frac{3c}{2r} \quad (3)$$

Relevant patents covering ultrasonic attenuation methods of particle size determination are U.S. Pat No. 3,799,070 (Cushman et al), U.S. Pat. No. 4,706,509 (Riebel and Loffler) and U.S. Pat. No. 5,121,629 (Alba). U.S. Pat. No. 3,799,070 describes the method used in the Autometrics PSM-400 analysers in which only two measurements are made, namely ultrasonic attenuation at two frequencies. The signals resulting are processed electronically to provide information on particle size and percent solids by volume in the slurry. U.S. Pat. No. 4,706,509 (Riebel and Loffler) effectively extends the Cushman et al patent by measuring the ultrasonic attenuation at a plurality of frequencies and so is able to derive a wider range of particle size data. U.S. Pat. No. 5,121,629 (Alba) also involves measuring ultrasonic attenuation over a selected frequency range. Alba describes various methods of deriving particle size distributions by comparing the measured and calculated attenuation spectra.

Figure 2:
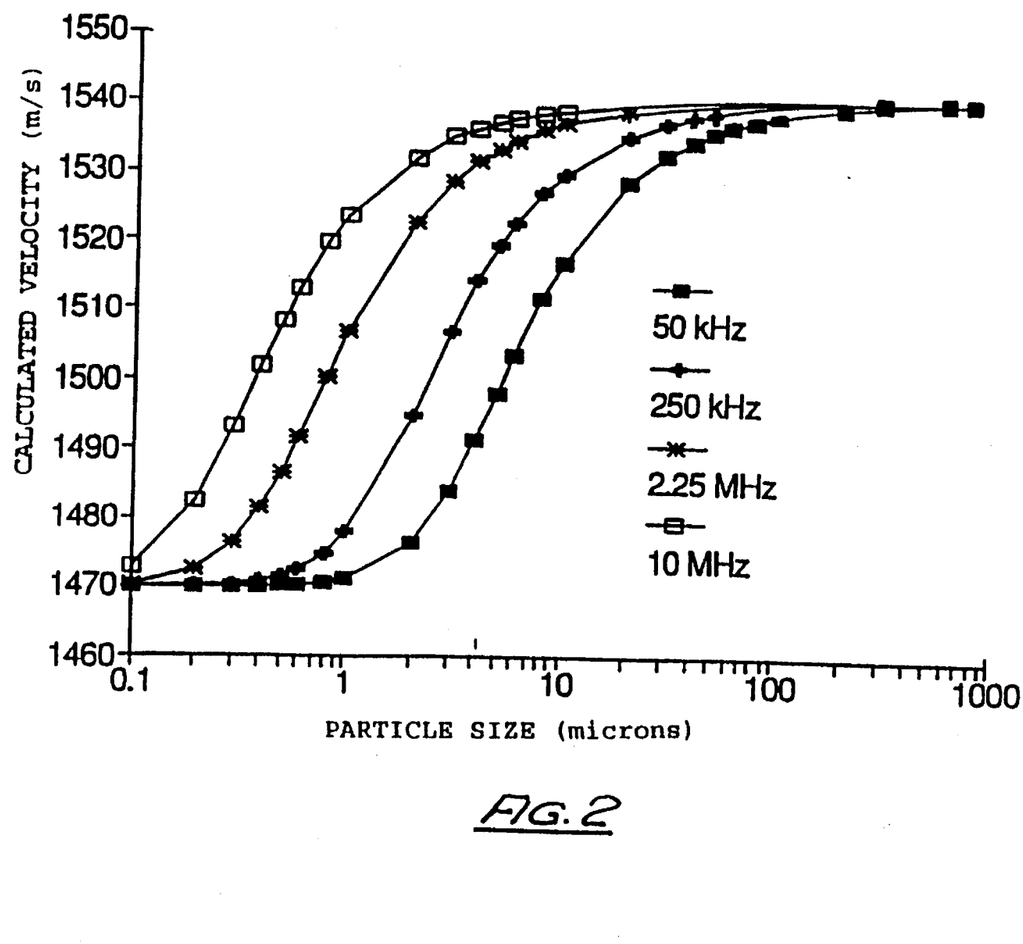
FIG. 2 is a graph showing the calculated velocity of ultrasound as a function of particle size and frequency for water containing 10% by weight of silica.

The velocity of ultrasound in suspensions has been shown by Harker and Temple (Journal of Physics D: Applied Physics 21 (1988) 1576–1588) to be a complex function of volume fraction, particle radius, fluid viscosity, frequency and compressibility. The effect of particles on the velocity of ultrasound in a suspension is best explained by an example. FIG. 2 shows the calculated velocity as a function of particle size for 10 wt % silica in water for various ultrasonic frequencies. For the larger particle sizes the wave propogation velocity is the same as that in the pure suspending fluid, although ultrasonic attenuation may be high. For the very small particle sizes, the particles tend to move in phase with the fluid in response to an ultrasonic wave. The suspension as a whole can be regarded as a continuum with respect to ultrasonic propagation. As a result, ultrasonic attenuation is very low, but the wave propagation velocity in the suspension may differ considerably from the wave propagation velocity in the pure suspending fluid. For intermediate fine particle sizes, between about 0.2 and 30 microns (for frequencies 50 kHz to 10 MHz), there are substantial velocity differences as a function of frequency. However, these velocity differences cannot be used to determine particle size without separate measurement of solids weight fraction and fluid characteristics.

DISCLOSURE OF THE INVENTION

It is an object of the present invention to provide an improved method and apparatus which avoids, or at least ameliorates, the above discussed disadvantages of the prior art. In particular, it would be desirable to measure several points on the particle size distribution curve of a suspension of alumina particles in a caustic solution of which the concentration of solute is variable. It would be especially desirable to determine particle size distribution on-line while avoiding the disadvantages of the prior art including the problem of scaling.

According to a first aspect of the invention there is provided a method for determining the particle size distribution of a suspension of solids in a solution bearing a solute, said method including the steps of:

(i) measuring the velocity of ultrasound on transmission through a sample of the solution;

(ii) measuring the attenuation of ultrasound on transmission through the sample;

(iii) measuring the attenuation of electromagnetic radiation on transmission through the sample to obtain a measure of the density of the sample;

(iv) deriving from the measure of density and the measure of said velocity an estimate of the concentration of solids in suspension;

(v) deriving from the measure of density and the measure of said velocity an estimate of the solute concentration; and (vi) deriving from the measures of ultrasonic attenuation, ultrasonic velocity and density a measure of particle size distribution.

Preferably, a measure of the fraction of particles in the sample of size less than about 20 microns is derived from the measurement of the difference in velocity of ultrasound transmission at two or more frequencies through the suspension in combination with the measurement of density and solute concentration. More preferably, the ultrasound transmission of higher frequency is used to provide the measure of ultrasonic velocity and, together with the measure of density, an estimate of the concentration of solids in suspension.

Preferably also, said measure of particle size distribution obtained in step (iv) is in respect of coarse particles only, that is, greater than about 30 microns.

According to a second aspect of the invention there is provided an apparatus for determining the particle size distribution of a suspension of solids in a solution bearing a solute, said apparatus including:

first means for providing a first signal indicative of the velocity of an ultrasound beam of predetermined frequency directed through a sample of the solution;

second means for providing a second signal indicative of the attenuation of ultrasound on transmission through the sample;

third means for measuring the attenuation of electromagnetic radiation on transmission through the sample and providing a third signal indicative of the density of the sample;

fourth means for deriving fourth and fifth respective signals indicative of the concentration of solids in suspension and the solute concentration from said first and third signals; and fifth means for deriving particle size distribution from said first, second and third signals.

According to a third aspect of the invention there is provided a method for determining the solids content of a suspension of solids in a solution bearing a solute, said method including the steps of:

(i) measuring the velocity of ultrasound on transmission through a sample of the solution;

(ii) measuring the attenuation of electromagnetic radiation on transmission through the sample to obtain a measure of the density of the sample; and (iii) deriving from the measure of the density and the velocity an estimate of the concentration of solids in suspension.

According to a fourth aspect of the invention there is provided an apparatus for determining the solids content of a suspension of solids in a solution bearing a solute, said apparatus including:

(i) means for measuring the velocity of ultrasound on transmission through a sample of the solution;

(ii) means for both measuring the attenuation of electromagnetic radiation on transmission through the sample and for producing a signal indicative of the density of the sample; and (iii) means for deriving signals indicative of the concentration of solids in suspension from the measurements of said density and said velocity.

According to a fifth aspect of the invention there is provided a method for determining the solute concentration of a suspension of solids in a solution bearing a solute, said method including the steps of:

(i) measuring the velocity of ultrasound on transmission through a sample of the solution;

(ii) measuring the attenuation of electromagnetic radiation on transmission through the sample to obtain a measure of the density of the sample; and (iii) deriving from the measure of density and the measure of said velocity an estimate of the solute concentration.

According to a sixth aspect of the invention there is provided an apparatus for determining the solute concentration of a suspension of solids in a solution bearing a solute, said apparatus including:

(i) means for measuring the velocity of ultrasound on transmission through a sample of the solution;

(ii) means for measuring the attenuation of electromagnetic radiation on transmission through the sample and producing a signal indicative of the density of the sample; and (iii) means for deriving signals indicative of the solute concentration from the signals indicative of said density and said velocity.

Typically, the electromagnetic radiation is provided by an X-ray or gamma-ray source. The following discussion will be directed to a gamma-ray source which by no means limits the scope of the present invention.

The ultrasound can be generated by transducer(s) which may have the ability to both transmit ultrasonic waves and receive them. Generally, the frequency of the ultrasound beam is in the range of 20 kHz to 20 MHz.

In a preferred embodiment, the ultrasonic transducers are attached to probes which contact the caustic solution. These probes protect the transducers from the solution, they allow a method for the correction of electronic and transducer drifts; they allow scale growth to be monitored by measuring the transit time of ultrasonic pulses reflected from the solid/liquid interface; and they allow the transmission distance in the suspension to be varied.

In a further preferred embodiment, the ultrasonic transducers and probes and the electromagnetic radiation transmission gauge are immersed in the process stream and are therefore referred to as immersion probes. Immersion probes have a number of significant practical advantages such as: the same probe design can be used for measurements at many different locations; the probes can be de-scaled by immersion in hot caustic; probe performance can be readily checked by immersion in standard solutions or suspensions; the probe can be calibrated by immersion in standard suspensions; and the distances between ultrasonic transmitters and receivers can be readily adjusted to achieve optimum performance.

The ultrasonic velocity can be measured by measuring the total ultrasound transit time through the suspension and probes and the probe reflection transit time of the transducers. The ultrasonic velocity $V_n$ can be determined by the following equation:

$$V_n = S_n/(T_n - R_n)$$

where $S_n$ is the path length in the suspension, corrected for scaling using the probe reflection transit times $R_n$. $T_n$ is the total ultrasound transmission transit time.

In a preferred embodiment, step (i) of the method further comprises the step of measuring the temperature of the sample. This can be achieved by placing a thermocouple into the suspension and generating a signal indicative of the temperature of the solution.

The equation for the determination of the solute concentration becomes:

$$C = a_0 + a_1 V_n + a_2 \rho + a_3 T$$

where $\rho = b_0 + b_1 ln(I/Io)$, $a_0, a_1, a_2, a_3, b_0, b_1$ are constants, $\rho$ is the density, I and Io are the gamma-ray intensities with and without the suspension respectively, and T is temperature.

The solids concentration W can be determined by the following equation:

$$W = c_0 + c_1 \rho + c_2 V_n$$

where $c_1, c_2, c_3$ are constants.

Particle size distribution $D_n$, as defined by a plurality of solids concentrations within various size intervals can then be determined by equations involving the ultrasonic attenuation measurements at various frequencies and the gamma-ray attenuation measurement, with corrections for the effects of caustic concentration, scaling, temperature and electronic drift. The equation used will involve linear combinations and ratios of the various measured parameters. For example, one equation for the determination of coarse particle size fractions from ultrasonic attenuation measurements at two frequencies ($A_1$ and $A_2$), density, velocity and temperature is:

$$D_n = d_0 + d_1(A_1/A_2) + d_2\rho + d_3/(A_2\rho) + d_4 V_1 + d_5 T$$

where $d_0, d_1, d_2, d_3, d_4$ and $d_5$ are constants.

For the fine particle size fractions, equations for the particle size distributions involve ultrasonic velocity measurements at low and high frequencies as well as gamma-ray attenuation and temperature. For example, an equation for the determination of fine particle size fraction $D_n$ from velocity measurements at low and high frequencies ($V_1$ and $V_h$), density and temperature is:

$$D_n = e_0 + e_1(V_h - V_1)/W + e_2\rho + e_3 V_h + e_4 T$$

where $e_1, e_2, e_3$ and $e_4$ are constants.

The effect of scaling is corrected by using the ultrasonic probe reflection transit time and the electronic drifts are corrected by the ultrasonic probe reflection amplitude.

The above equations can be solved by entering the relevant data (or signals indicative thereof) into a programmable computer.

Typically, the solute is caustic soda and the suspension is alumina, although the invention is equally applicable to other suspensions.

The method, in a preferred form, involves the following measurements:

(a) ultrasonic transmission attenuation at a number of ultrasonic frequencies generally within the range 20 kHz to 20 MHz ($A_1, A_2, \ldots$);

(b) total ultrasonic transmission transit time in the probes and suspension at each frequency ($T_1, T_2, \ldots$);

(c) ultrasonic probe reflection amplitude at each frequency ($P_1, P_2, \ldots$);

(d) ultrasonic probe reflection transit time at each frequency ($R_1, R_2, \ldots$);

(e) gamma-ray attenuation in the suspension (I/Io) where I and Io are the gamma-ray intensities with and without the suspension respectively; and (f) temperature of the suspension (T).

Advantageously, means are included to remove or stabilise the entrained air in the sample being measured.

Agitation means may also be provided to establish and maintain substantially uniform particle suspension in the slurry.

Optionally, pulse-echo techniques rather than transmission techniques can be used. In pulse-echo operation, the ultrasonic transmitters are also used as receivers with sound reflector(s) being arranged opposite the ultrasonic transmitters in the measurement sections.

The advantages of preferred embodiments of the measurement system of the invention are: that analysis can be performed rapidly; measurements can be performed directly in process streams; sampling problems are minimised as a bulk analysis is made of the suspension using ultrasonic path lengths of about 50 to 300 mm; the process is unaffected; and multiple points on the size distribution curve can be monitored.

BRIEF DESCRIPTION OF THE DRAWINGS

A preferred embodiment of the invention will now be described, by way of example only, with reference to the following drawings in which:

FIG. 6b is a sectional view taken along line 6b—6b of FIG. 6a.

MODES FOR CARRYING OUT THE INVENTION

The invention in one preferred embodiment will now be described, by way of example only, with reference to the following examples.

EXAMPLE 1

(a) Samples

Seventeen particulate samples were used to test and demonstrate the method of the present invention. The samples comprised 7 commercially available alumina powder samples, 3 alumina trihydrate samples from Queensland Alumina Limited (QAL), 6 crystalline silica samples and 4 glass microsphere samples. The particle size of these samples were previously determined by a Malvern laser particle size analyser at the University of New South Wales. The d50 of these samples ranged from 5.9 to 210 microns.

(b) Slurries

The above samples were mixed with caustic solutions of concentrations from 150 to 250 g/l NaOH and synthetic Bayer liquors of caustic concentrations 113 and 189 g/l NaOH. The synthetic Bayer liquors had alumina to caustic ratios of 0.35 and 0.40.

(c) Experimental Apparatus

Figure 3:
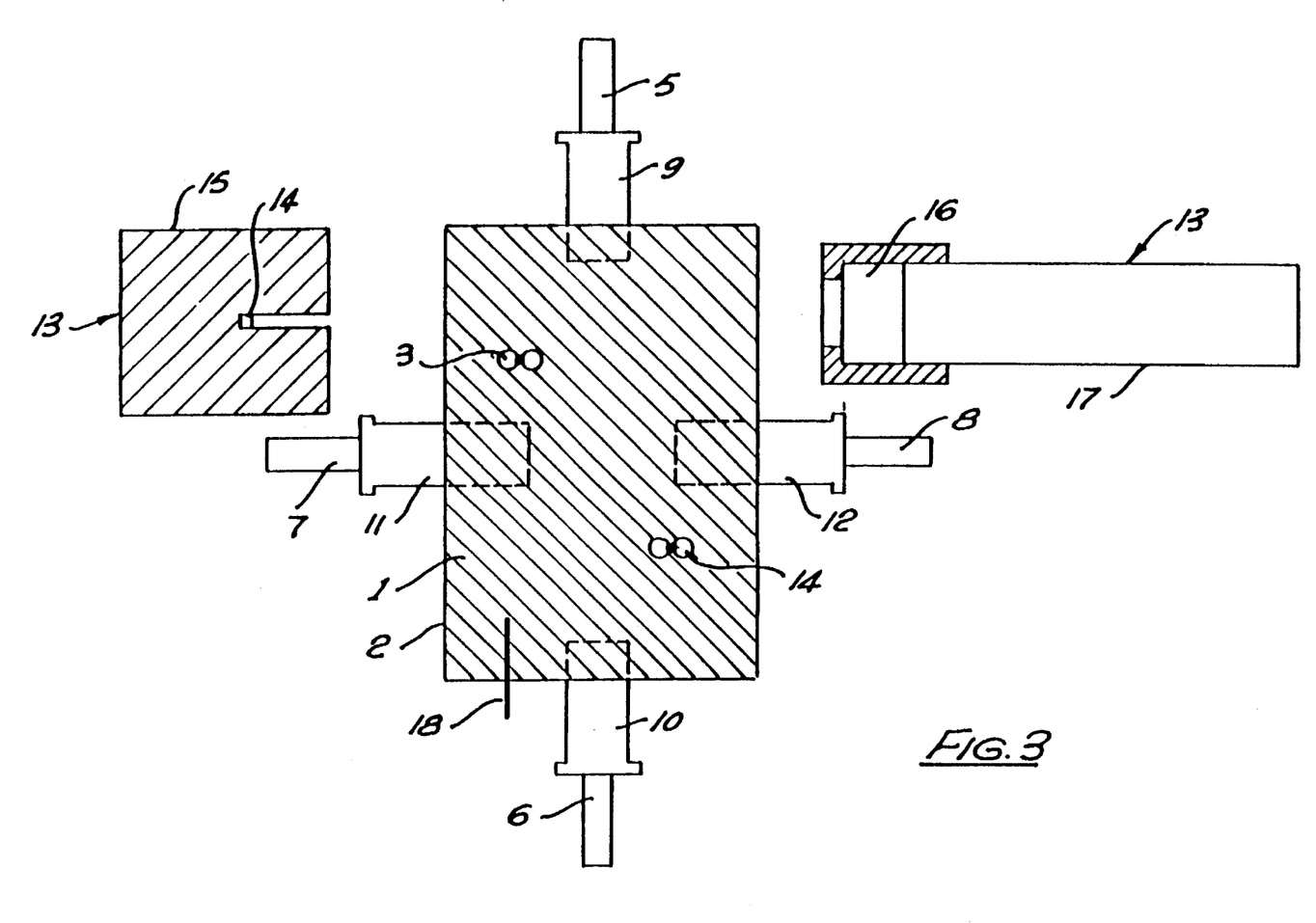
FIG. 3 is a schematic diagram of a device according to the present invention for on-line particle size measurement, where the device includes four pairs of ultrasonic transducers and a gamma-ray transmission gauge.
Figure 4:
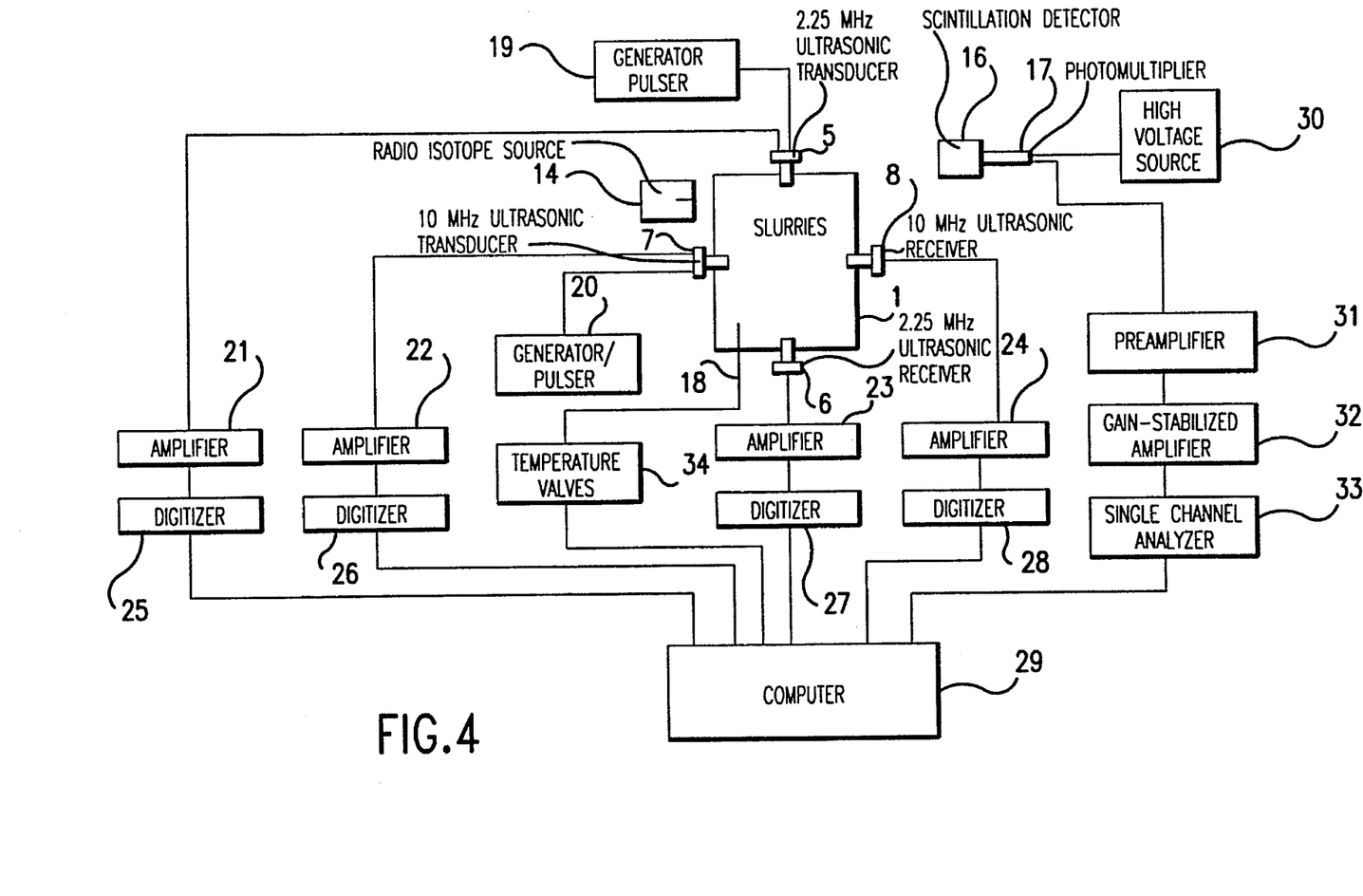
FIG. 4 is a schematic diagram of the device of FIG. 3 as configured in the laboratory to determine the ultrasonic particle size analysis.

Referring to FIGS. 3 and 4, the above slurries 1 were placed in a stainless steel vessel 2 of 5 liter capacity as shown in FIG. 3. The vessel 2 was located on a heating plate (not shown) so that the temperature of the slurry could be raised to over 80° C. Stirrers 3 and 4 in the vessel were used to keep the solids in suspension without introducing air into the slurry.

The apparatus included two pairs of ultrasonic transducers, a 2.25 MHz ultrasonic transmitter/receiver 5, a 2.25 MHz ultrasonic receiver 6, a 10 MHz ultrasonic transmitter/receiver 7 and a 10 MHz ultrasonic receiver 8, which were connected to probes 9, 10, 11 and 12 respectively which contacted the slurry 1. Machinable ceramic was found to be a suitable material for these probes, combining a low temperature coefficient for both ultrasonic attenuation and velocity with a moderate attenuation to minimise "ringing".

The apparatus also incorporated a $^{137}$Cs gamma-ray transmission gauge 13 having a 370 mBq (10 mCi) $^{137}$Cs radioisotope source 14, a lead shield 15 and a NaI(Tl) scintillation detector (50×50 mm) 16 coupled with a photomultiplier tube 17. A thermocouple 18 was also placed into the slurry to measure the temperature of the suspension.

Signals were generated by the generator/pulsers, 19 and 20 as shown in FIG. 4 and transmitted through the slurry 1. Attenuated signals were then received by the transducers, 5, 6, 7 and 8 and amplified by amplifiers 21, 22, 23 and 24, digitised by digitisers 25, 26, 27, 28 and fed into a computer 29. Gamma-rays were also transmitted from source 14 and detected by the scintillation detector 16, the photomultiplier tube 17 being powered from high voltage source 30. The signals thus detected were then fed through a preamplifier 31, a gain-stabilised amplifier 32, a single channel analyser 33 and fed into computer 29. Temperature was also measured using the thermocouple 18 and the temperature values 34 were also fed into computer 29.

(d) Results

In the first set of experimental data, 14 samples (excluding the three QAL samples) were measured in caustic solutions over a range of caustic concentrations (150 to 250 g/l), solid fractions (5 to 20 wt %) and temperatures (22° to 35° C.). This first data set comprised 80 sets of measurements.

Figure 7:
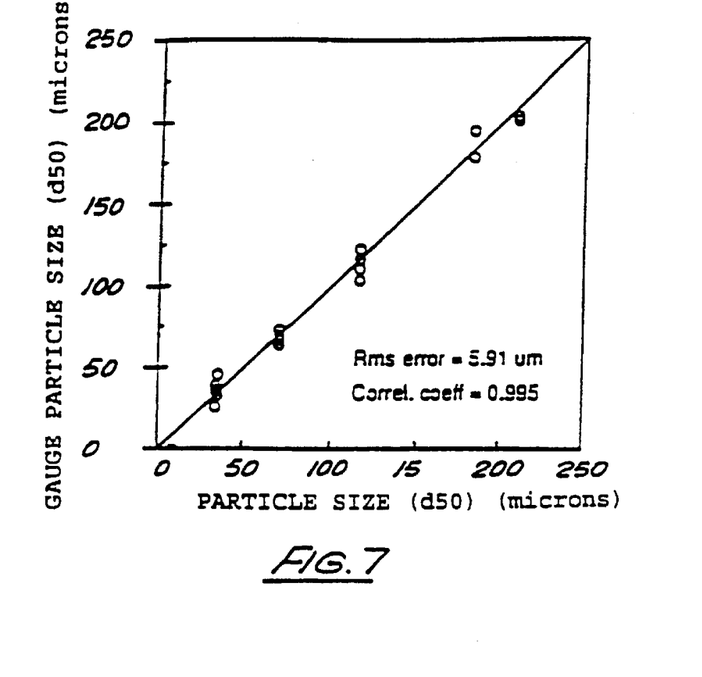
FIG. 7 is a graph of particle size (d50) determined by a Malvern laser diffraction instrument versus the particle size measured by the gauge in FIGS. 3 and 4 for samples of 5 and 10 wt % solids.

The accuracy of determination of particle size (d50), sample mass and caustic concentration is given in Table 1 and FIG. 7. The results show that d50 can be measured to within 5.9 μm (one standard deviation) provided that the solids fraction is below about 12 wt %.

The errors in particle size determinations would be lower for a less diverse range of samples to those used in the present experiments.

TABLE 1

| | | Range of Conditions in Laboratory Experiments | | |
|---|---|---|---|---|
| Parameter | Rms error | d50 (μm) | Caustic (g/l NaOH) | Solids fraction (wt %) |
| d50 | 3.8 μm | 33–98 | 113–188 | 10–30 |
| | 5.9 μm | 7–210 | 150–250 | 5–10 |
| % >40 μm | 0.97 wt % | 91–100 wt %* | 113–250 | 24–30 |
| Caustic | 1.32 g/l | 33–98 | 113–188 | 3–30 |
| | 3.78 g/l | 7–210 | 150–250 | 5–20 |
| Solids | 0.49 wt % | 33–98 | 113–188 | 3–30 |
| fraction | 0.68 wt % | 7–210 | 150–250 | 5–20 |

*Range of fraction above 40 μm (wt %)

Figure 8:
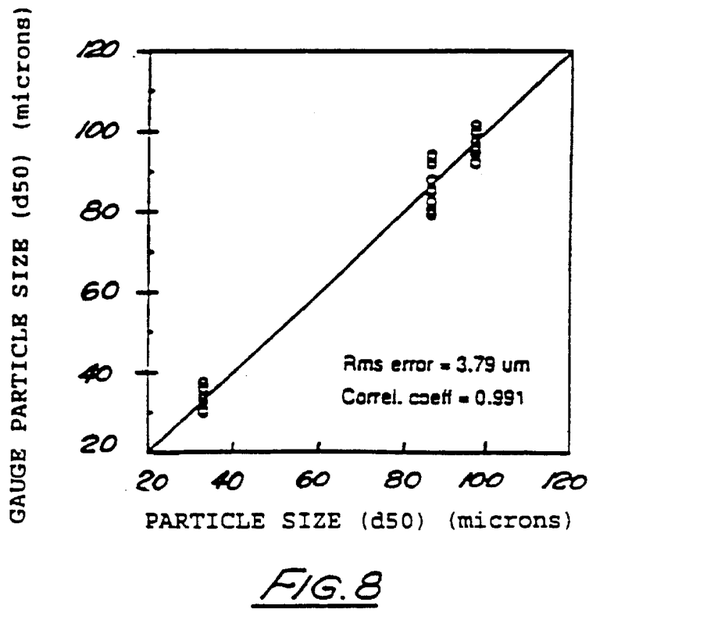
FIG. 8 is a graph showing the determination of particle size (d50) using the gauge in FIGS. 3 and 4 for alumina samples of 10 to 30 wt % solids in synthetic Bayer liquors.
Figure 9:
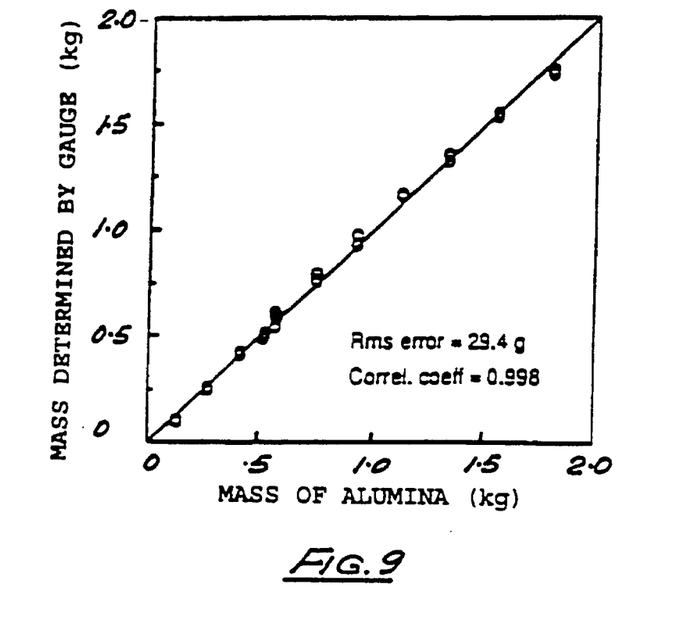
FIG. 9 is a graph showing the determination of the mass of alumina added to synthetic Bayer liquors using the gauge in FIGS. 3 and 4.

In a second set of experimental data, three alumina hydrate samples were measured in four synthetic Bayer liquors at solids fractions from 3 to 30 wt %. The results of these measurements are shown in Table 1 and in FIGS. 8 and 9. In FIG. 9, a mass of 1.8 kg is equivalent to a solids fraction of 30 wt %.

The results for particle size (d50) show that d50 can be determined to within an rms error of 3.79 μm for solids fractions between 10 and 30 wt %. Including the points at 6 and 9 wt % solids increases the rms error to 5.5 μm.

Alternatively, the particle size data can be analysed in terms of the fraction greater than a particular size. Analysis of six samples with between 91% and 100% greater than 40 microns showed that the fraction greater than 40 microns could be determined to within 0.97 wt % for the range of conditions shown in Table 1.

Figure 10:
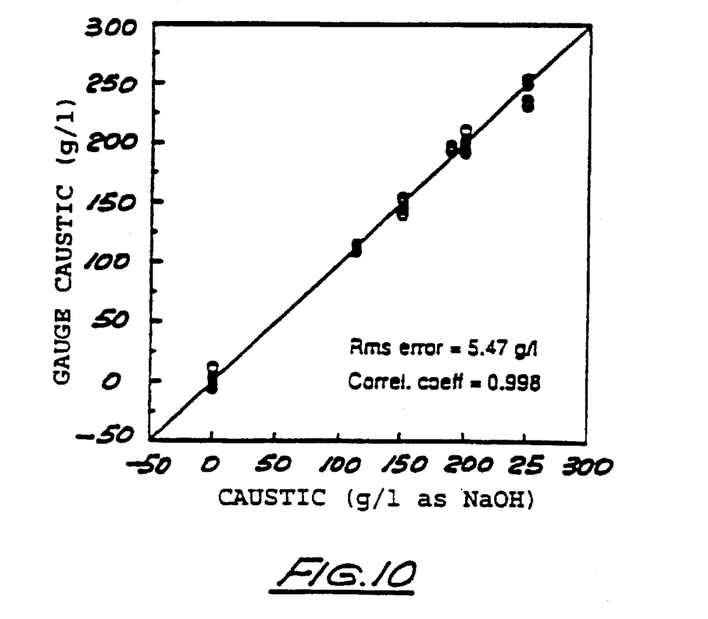
FIG. 10 is a graph showing the determination of caustic concentration using the gauge in FIGS. 3 and 4 for synthetic Bayer liquors, NaOH solutions and water.

The results for the determination of caustic concentration based on ultrasonic velocity and γ-ray density show that for the synthetic Bayer liquors alone, caustic concentration can be determined to within 1.17 g/l. Combining all the solution runs (i.e. no particulates) on synthetic Bayer liquors, caustic and water shows that the caustic concentrations can be determined to within 5.47 g/l (FIG. 10).

Ultrasonic velocity is strongly affected by caustic concentration. For example, at 200 g NaOH per liter, a 2 g/l increase in caustic concentration increases the velocity of ultrasound by 2.2 m/s. However, ultrasound velocity is not strongly affected by temperature, the change being only about −0.6 m/s per ° C. at 2.25 MHz and −0.44 m/s per ° C. at 10 MHz.

Typical terms in the equations used to determine particle size, solids fraction and caustic concentration are given in Table 2.

TABLE 2

|  | Parameter (Y) | | | |
| --- | --- | --- | --- | --- |
| Typical terms in equation* | Solids fraction or sample mass | Particle size (d50) | Particle size (% > than 40 μm) | Caustic Concentration |
| $X_1$ | $\rho$ | $A_1 A_2$ | $A_1/A_2$ | $\rho$ |
| $X_2$ | $V_1$ | $1/(A_2 \cdot m)$ | $\rho$ | $V_1$ |
| $X_3$ |  | $A_1$ | $V_1$ |  |
| $X_4$ |  | $V_1$ |  |  |

*The parameters (Y) were determined using equation so the form $Y = a_0 + a_1 X_1 + a_2 X_2 + a_3 + a_4 X_4$ where $a_0 \ldots a_4$ are constants and $X_1 \ldots X_4$ are listed in the Table. $A_1$, $A_2$ = corrected ultrasonic amplitude at 2.25 and 10 MHz respectively and $V_1$ = measured velocity of 2.25 MHz ultrasound in the suspension.

EXAMPLE 2

An additional set of measurements were obtained to examine the feasibility of using ultrasonic velocity techniques to determine fine fractions independent of the larger size fraction concentrations. Laboratory experiments were carried out using six silica samples with fractions finer than 10 microns ranging from 20 and 53 wt %. The samples were mixed with water at solids loadings of 5, 10 and 20 wt %.

Figure 11:
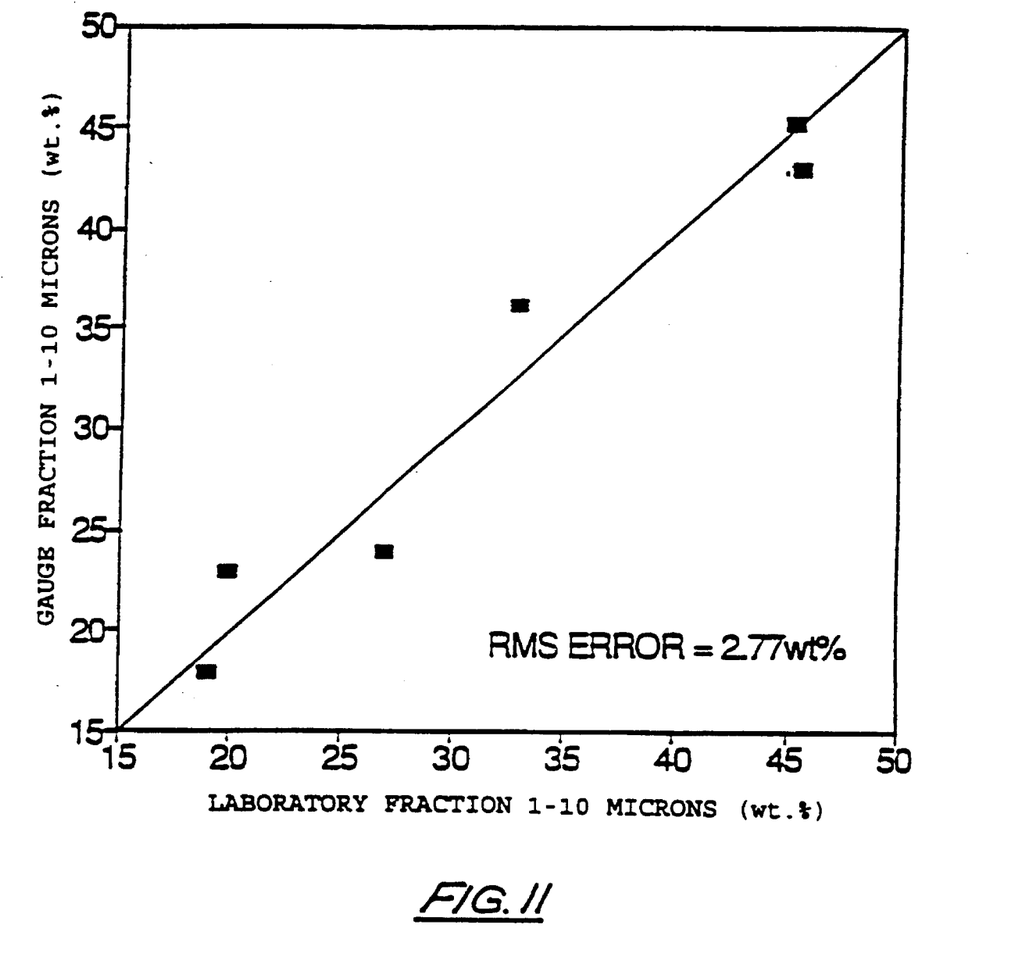
FIG. 11 is a graph showing the determination of the fines fraction (1–10 microns) in six silica samples in water, each containing 10 wt % solids. Gauge determination was based on measurement of ultrasonic velocities at 250 kHz and 10 MHz.

Ultrasonic velocities were measured at the frequencies of 250 kHz and 10 MHz to determine the fines fractions in the samples. The results obtained are illustrated graphically in FIG. 11 and are accurate to better then 3 wt % for constant solids loading. This error rises to approximately 5 wt % for variable solids loading.

In agreement with the calculated values displayed in FIG. 2, the velocity of the 10 MHz ultrasound at constant solids fraction was essentially constant for the varying particle size while the velocity of the 250 kHz ultrasound decreased substantially linearly with increasing fine fraction.

Figure 5:
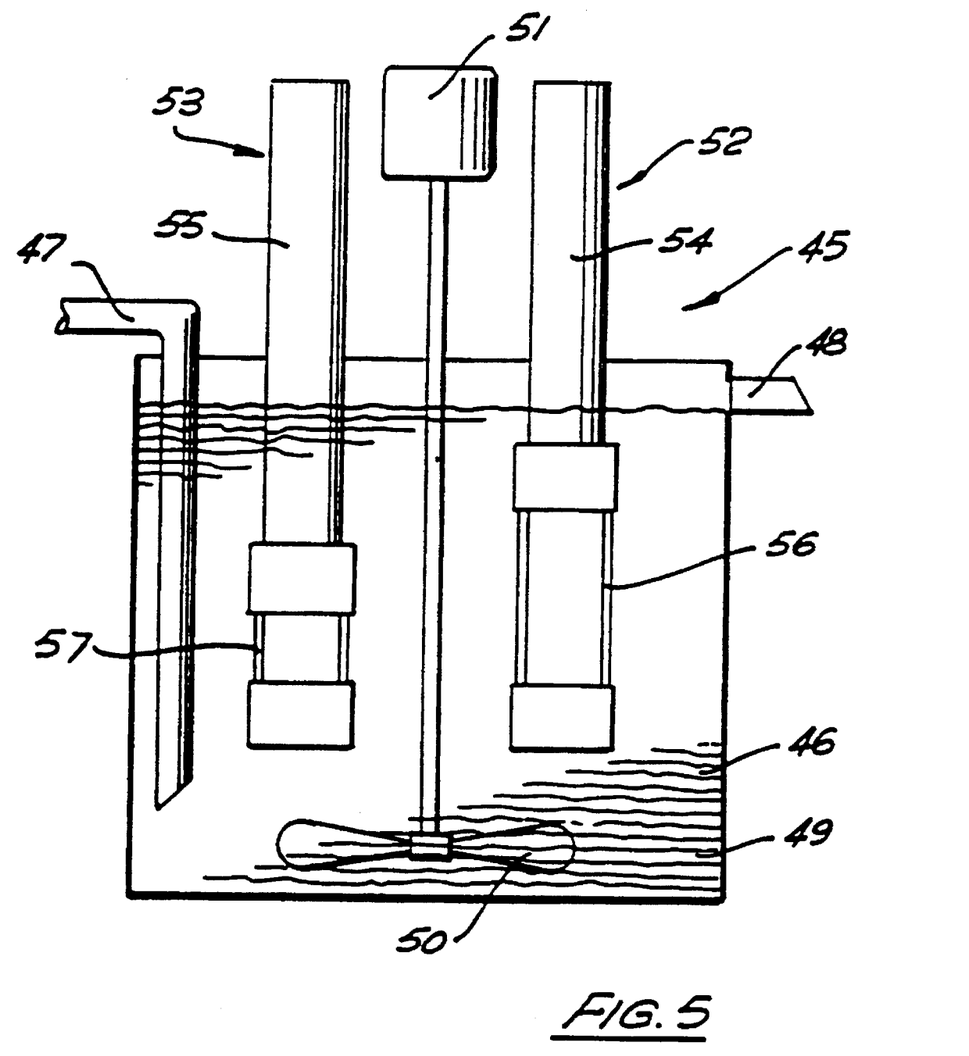
FIG. 5 is a schematic cross-sectional view of an immersion probe measurement system used to obtain the ultrasonic particle size analysis.
Figure 6A:
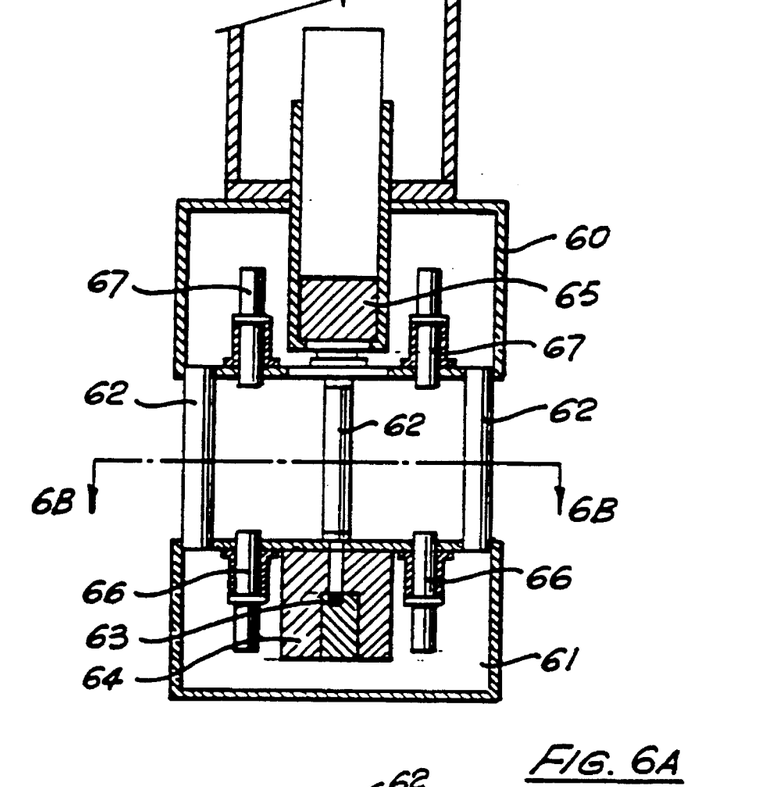
FIG. 6a is a cross-sectional view of the low frequency immersion probe of FIG. 5.
Figure 6B:
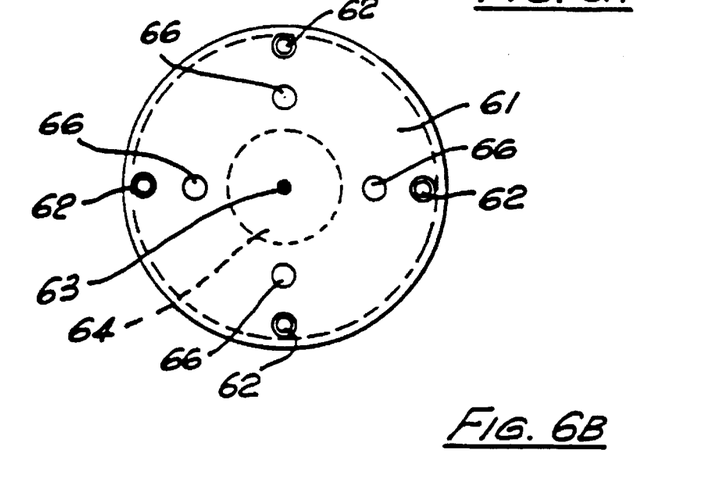

Referring now to FIGS. 5, 6a and 6b there is illustrated a schematic representation of a measurement system 45 as envisaged by the present invention. The system includes a tank 46 having an inlet and outlet 47 and 48 through which a sample 49 flows prior and subsequent to measurement.

System 45 also includes a stirrer 50 which is disposed near the base of tank 46 and driven by a motor 51 for maintaining a well mixed solution within the tank. Two immersion probes 52 and 53 extend downwardly into the tank and include respective support tubes 54 and 55, and sensor portions 56 and 57. Preferably, portions 56 and 57 are disposed approximately mid-way between the top and base of tank 46, however, satisfactory operation is achieved while these portions are completely immersed in sample 49. Probes 52 and 53 are respectively configured to measure low and high frequency ultrasound velocity through the sample.

An enlarged cross-sectional view of probe 53 is illustrated in FIGS. 6a and 6b. Sensor portion 57 includes two axially spaced apart tubular bases 60 and 61 which are connected by way of four peripherally located and axially extending tubes 62. Base 61 includes a centrally mounted radioactive source 63 contained within a storage shield 64. Opposing source 63 is a gamma ray detector 65 located within base 60.

Base 61 also includes four equally angularly spaced ultrasonic transducers 66 which are radially offset from source 63. Base 60 includes four similar transducers 67 which are each disposed immediately above one of respective transducers 66.

It will be appreciated that tube 62 preferably communicates with the interior of both bases 60 and 61 so that any water or power supply lines can extend therethrough. Preferably also, the cables carrying the signals provided by transducers 66 are also ducted through one of tubes 62.

It will be understood that the velocity of ultrasound transmission through a sample can be measured in other ways without departing from the scope of the invention. The velocity can be compared with the velocity obtained using calibration samples or the caustic concentration can be calculated from a knowledge of the constants preferably by use of analogue or digital computation equipment.

Likewise the density measurements can be derived from the γ-radiation attenuation by calibration or by calculation from a knowledge of the constants.

Although the foregoing describes specific embodiments of the invention, other modifications apparent to the skilled addressee fall within the scope of the invention.

I claim:

1. A method of determining the particle size distribution of a suspension of solids in a solution bearing a solute, said method including the step of:

(i) measuring the velocity of ultrasound on transmission through a sample of the solution;

(ii) measuring the attenuation of ultrasound on transmission through the sample;

(iii) measuring the attenuation of electromagnetic radiation on transmission through the sample to obtain a measure of the density of the sample;

(iv) deriving from the measure of density and the measure of said velocity an estimate of the concentration of solids in suspension;

(v) deriving from the measure of density and the measure of said velocity an estimate of the solute concentration; and (vi) deriving from the measure of ultrasonic attenuation, ultrasonic velocity and density the measure of particle size distribution.

2. A method according to claim 1, wherein the temperature of the sample is variable, said method further including the step of measurement of the temperature of the sample.

3. A method according to claim 1 further comprising the steps of measuring the velocities of ultrasound transmissions of at least two different frequencies through the suspension and deriving the fraction of particles of size less than 20 μm in the suspension from said measured velocities of ultrasound transmission, the measured density of the suspension, and the measured solids concentration of the suspension.

4. A method according to claim 3 wherein a measurement of the concentration of solids in suspension is derived from the measured velocity of the highest frequency ultrasound transmission through the suspension and the measured density of the suspension.

5. A method according to claim 1 wherein the ultrasonic velocity is measured by obtaining the ultrasound transit time and probe reflection amplitudes from spaced apart ultrasonic transducers.

6. A method according to claim 1 wherein the solute is caustic soda.

7. A method according to claim 1 wherein the solid is alumina.

8. An apparatus for determining the particle size distribution of a suspension of solids in a solution bearing a solute, said apparatus including:

first means for providing a first signal indicative of the velocity of an ultrasound beam of predetermined frequency directed through a sample of the solution;

second means for providing a second signal indicative of the attenuation of ultrasound on transmission through the sample;

third means for measuring the attenuation of electromagnetic radiation on transmission through the sample and providing a third signal indicative of the density of the sample;

fourth means for deriving fourth and fifth respective signals indicative of the concentration of solids in suspension and the solute concentration from said first and third signals; and     fifth means for deriving particle size distribution from said first, second and third signals.

9. An apparatus according to claim 8 wherein said first means also provides a sixth signal indicative of the velocity of another ultrasound beam of differing frequency for providing a measure of the fraction of particles in said sample of a size less than about 20 microns.

10. An apparatus according to claim 9 wherein said fifth means derives the fraction of particles in said sample of size less than about 20 microns from first and third signals.

11. An apparatus according to claim 10 wherein said predetermined frequency is greater than said differing frequency.

12. A method for determining the solids content of a suspension of solids in a solution bearing a solute, said method including steps of:

(i) measuring the velocity of ultrasound on transmission through a sample of the solution; (ii) measuring the attenuation of electromagnetic radiation on transmission through the sample to obtain a measure of the density of the sample; and     (iii) deriving from the measure of the density and the velocity an estimate of the concentration of solids in suspension.

13. An apparatus for determining the solids content of a suspension of solids in a solution bearing a solute, said apparatus including:

(i) means for measuring the velocity of ultrasound on transmission through a sample of the solution;

(ii) means for both measuring the attenuation of electromagnetic radiation on transmission through the sample and for producing a signal indicative of the density of the sample; and     (iii) means for deriving signals indicative of the concentration of solids in suspension from the measure of said density and said velocity.

14. A method for determining the solute concentration of a suspension of solids in a solution bearing a solute, said method including the steps of:

(i) measuring the velocity of ultrasound on transmission through a sample of the solution;

(ii) measuring the attenuation of electromagnetic radiation on transmission through the sample to obtain a measure of the density of the sample; and (iii) deriving from the measure of density and the measure of said velocity an estimate of the solute concentration.

15. An apparatus for determining the solute concentration of a suspension of solids in a solution bearing a solute, said apparatus including:

(i) means for measuring the velocity of ultrasound on transmission through a sample of the solution;

(ii) means for measuring the attenuation of electromagnetic radiation on transmission through the sample and producing a signal indicative of the density of the sample; and     (iii) means for deriving signals indicative of the solute concentration from the signals indicative of said density and said velocity.

* * * * *

UNITED STATES PATENT AND TRADEMARK OFFICE
CERTIFICATE OF CORRECTION

PATENT NO. : 5,569,844
DATED : October 29, 1996
INVENTOR(S) : Brian D. Sowerby

It is certified that error appears in the above-indentified patent and that said Letters Patent is hereby corrected as shown below:

| Column | Line | |
|---|---|---|
| 2 | 32 | After "use." start new paragraph. |
| 11 | 35 | After "at the" do not start new paragraph. |
| 13 | 38 | After "solution;" start new paragraph. |
| 14 | 24 | After "sample; and" start new paragraph. |

Signed and Sealed this

Eighteenth Day of February, 1997

Attest:

BRUCE LEHMAN

Attesting Officer   Commissioner of Patents and Trademarks